United States Patent [19]

Landry

[11] E Patent Number: Re. 33,234

[45] Reissued Date of Patent: Jun. 19, 1990

[54] TRANSCUTANEOUS INTRAVENOUS ILLUMINATOR

[76] Inventor: Kim Landry, 4345 SW. 20th La., Gainsville, Fla. 32607

[21] Appl. No.: 230,061

[22] Filed: Aug. 8, 1988

Related U.S. Patent Documents

Reissue of:

[64] Patent No.: 4,619,249
Issued: Oct. 28, 1986
Appl. No.: 758,399
Filed: Jul. 24, 1985

[51] Int. Cl.[5] ..... A61B 1/06

[52] U.S. Cl. ..... 128/23; 128/397; 128/20; 362/199

[58] Field of Search ..... 128/23, 395, 396, 397, 128/398, 9, 1.3, 1.4; 604/19, 20, 21; 362/32, 199

[56] References Cited

U.S. PATENT DOCUMENTS

| | | | |
|---|---|---|---|
| 604,949 | 5/1898 | Wappler | 128/23 X |
| 1,231,702 | 7/1917 | Cameron | 128/16 |
| 1,662,150 | 3/1928 | Kerr | 128/23 |
| 2,161,688 | 6/1939 | Schwartz | 128/23 |
| 2,186,143 | 1/1940 | Neugass | 128/16 |
| 2,247,258 | 6/1941 | Shepard | 128/16 |
| 3,195,536 | 7/1965 | Hovananian et al. | 128/6 |
| 3,527,932 | 9/1970 | Thomas | 128/23 X |
| 3,614,414 | 10/1971 | Gores et al. | 240/2 |
| 3,664,330 | 5/1972 | Duetsch | 128/18 |
| 4,052,980 | 10/1977 | Grams et al. | 128/18 |
| 4,060,724 | 11/1977 | Heine | 128/398 X |
| 4,112,923 | 9/1978 | Tomecek | 128/395 X |
| 4,265,227 | 5/1981 | Ruge | 128/23 |
| 4,286,602 | 9/1981 | Guy | 128/23 X |
| 4,312,357 | 1/1982 | Andersson et al. | 128/23 X |
| 4,495,949 | 1/1985 | Stoller | 128/23 X |
| 4,539,987 | 9/1985 | Nath et al. | 128/398 X |
| 4,556,052 | 12/1985 | Muller | 128/11 |
| 4,597,030 | 6/1986 | Brody et al. | 362/32 |

*Primary Examiner*—William H. Grieb
*Attorney, Agent, or Firm*—Pravel, Gambrell, Hewitt, Kimball & Krieger

[57] ABSTRACT

A transcutaneous illuminating apparatus comprising: a housing having a source of electrical energy provided therein, a support removably mounted on one end of the housing having a plurality of arms pivotally supported thereby at their proximate ends, each of the arms having mounted on its distal end illuminating lights, an electrical circuit including the source of power and the illuminating lights, a switch for selectively completing the circuit between the illuminating lights and the source of electrical energy thereby activating the illuminating lights, and rheostats provided in the circuit for selectively varying the intensity of each of the illuminating lights.

17 Claims, 2 Drawing Sheets

TRANSCUTANEOUS INTRAVENOUS ILLUMINATOR

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to diagnostic illuminating instruments, and more particularly to a transcutaneous intravenous illuminating apparatus to allow visualization of veins that are otherwise difficult to see or palpate.

2. General Background

If a small beam of light is held flush against the skin some of the light penetrates, scatters and illuminates a small area under the skin. There are peripheral veins that are dense and therefore do not absorb light very well. These veins can be readily identified in the illuminated field. The concept of using a small directed beam of light to illuminate a peripheral vein can be demonstrated using the proper light source. Since dark skin absorbs more light than light skin, a higher intensity light is required to achieve this same effect. Thus the need for an illuminating instrument which will allow visualization of peripheral veins that are otherwise difficult to see or palpate.

Different patents directed to the use of a light beam to perform transcutaneous inspections on living organs and tissue have been issued.

U.S. Pat. No. 4,112,923 issued to J. J. Tomecek entitled "Antonomic Transcutaneous Affect Device" discloses a device for performing transcutaneous inspections of preselected areas of living organs and tissue utilizing light. The apparatus has a self-contained power supply in a housing, a probe circuit to detect points of high and/or low resistance in the organism, and audible signal for indicating that such points have been realized, and a treatment circuit which applies light to the detected point.

U.S. Pat. No. 3,527,932 issued to J. J. Thomas entitled "Transilluminating Flashlight" discloses a portable battery operated flashlight having a tubular hole extending beyond the light emitting end of a flashlight to perform transcutaneous inspection on a baby's head to look at the brain formation.

U.S. Pat. No. 4,495,949 issued to M. Stoller entitled "Transillumination Method" discloses a testing technique in which a multi-wavelength light beam containing different colors is passed through tissue and divided and filtered to provide plural light beams lying in separate wavelength ranges which are detected by a video system which provides information bearing signals to data processing circuitry which determines the transmissivity at each wavelength of each point of the object within the viewing field.

U.S. Pat. No. 4,312,357 issued T. Andersson, et al. entitled "Transillumination Diagnostic Method and Apparatus" discloses the use of multiple light emitters for inspecting parts of the body. The first light emitter has a tungsten filament which transilluminates the tissue and the second light emitter emits a light of higher intensity than the first emitter and is actuated while the tissue is being transilluminated by the first light emitter to make an exposure on infrared sensitive film located at the opposite end of the tissue.

U.S. Pat. No. 4,265,227 issued to W. Ruge, U.S. Pat. No. 1,662,150 issued to C. H. Kerr, U.S. Pat. No. 4,286,602 issued to R. Guy, and U.S. Pat. No. 4,060,724 issued to H. A. Heine, et al. all disclose apparatus which use a light beam to perform inspection of parts of the body.

3. Summary of the Invention

The present invention solves the prior art problems and shortcomings in a simple and inexpensive straightforward manner. The present invention provides a transcutaneous illuminating apparatus having a housing with a source of electrical energy provided therein, a means removably mounted on one end of the housing having a plurality of tubular members pivotally attached thereto and supporting at each of their termini illuminating means thereon, means for selectively opening and closing a circuit between the illuminating means and said source of electrical energy thereby activating and deactivating the illuminating means, means for selectively adjusting the intensity of each of the illuminating means, and means for applying each of the illuminating means to the tissue area to be inspected.

Thus, it is an object of the present invention to provide a light source which allows visualization of peripheral veins which are otherwise difficult to see or palpate.

It is a further object of the present invention to save a patient the agony of being stuck with needles repeatedly until a vein is found.

It is a further object of the present invention to allow the ready location of a large peripheral vein over a smaller easy-to-palpate one.

It is a further object of the present invention to locate alternate insertion sites on patients frequently receiving intravenous injections.

It is a further object of the present invention to reduce the amount of time needed to start a difficult intravenous connection thereby allowing other procedures to be done.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
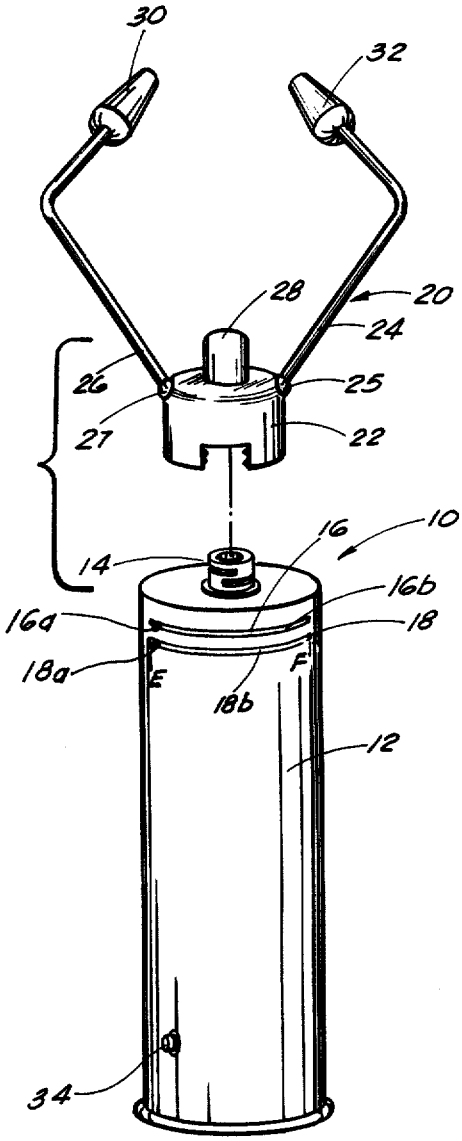
FIG. 1 is a rear elevational view of the preferred embodiment of the apparatus of the present invention.

FIG. 1 best illustrates the preferred embodiment of the apparatus of the present invention designated generally by the numeral 10. In FIG. 1 there can be seen a cylindrical housing 12 defining a hollow interior in which is stored a source of electrical energy (not shown) such as a conventional battery. Housing 12 is provided with a standard otoscope neck 14 which is adapted to threadably receive head portion 20 of transcutaneous illuminator apparatus 10.

Head portion 20 of transcutaneous illuminator apparatus 10 is comprised of a base portion 22 having pivotally mounted thereto a plurality of curvilinear tubular members or arms 24, 26 connected to base portion 22 at ball or swivel joints 25, 27 respectively. To the preferred embodiment 10 optional conventional locking mechanisms may be provided to ensure the orientation of tubular members 24, 26 with respect to base portion 22 is maintained. Tubular members or arms 24, 26 have provided at the distal ends thereof illuminating means or lamps 31, 33 provided with hoods 30, 32 respectively for maximum contrast. Typical transilluminators would be Nos. 43000 and 43200 manufactured by Welch Allyn. Lamps 31, 33 are preferably halogen lights with fiber optics and are connected to a circuit including the source of electrical power (not shown) and a means for completing the circuit, and thereby activating lights 31, 33, such as rheostat switches 16a, 18a. A pen light (not shown) can be provided in a socket in shield 28 and be connected to the source of electrical energy to provide illumination, when activated by depressing switch or button 34, for the area to be worked as will be described further herein.

Provided on exterior of housing 12 is a pair of rheostats 16, 18 which activate, deactivate and vary the intensity of lamps 31, 33. Each of rheostats 16, 18 is provided with a trigger 16a, 18a provided in slots 16b, 18b respectively in housing 12 such that triggers 16a, 18a are selectively movable along slots 16b, 18b between POINT E to deactivate lamps 31, 33 respectively (POINT E being the "off" position) and a POINT F of maximum intensity of lamps 31, 33 respectively. The rheostats 16, 18 independently control lamps 31, 33 respectively so that the intensity of each can be separately varied.

Figure 2:
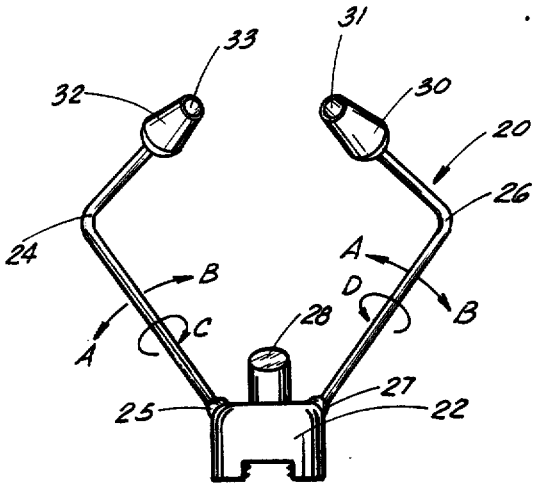
FIG. 2 is a frontal elevational view of the upper portion of the preferred embodiment of the apparatus of the present invention.
Figure 3:
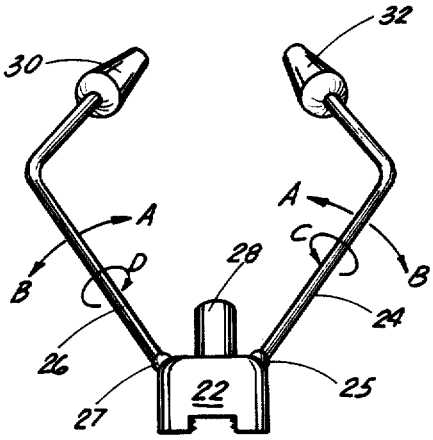
FIG. 3 is a rear elevational view of the upper portion of the preferred embodiment of the apparatus of the present invention.
Figure 4:
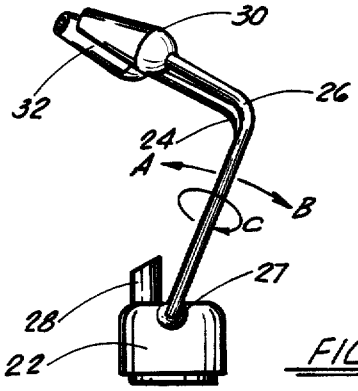
FIG. 4 is a side elevational view of the upper portion of the preferred embodiment of the apparatus of the present invention.

As best seen in FIGS. 2–4 each of lamps 31, 33 provided on pivotal tubular members or arms 24, 26 respectively are movable about joints 25, 27 respectively. Movement of arms 24, 26 can be forward in the direction of ARROW A, rearward in the direction of ARROW B or circularly in the direction of ARROWS C or D depending on operational needs.

Figure 6:
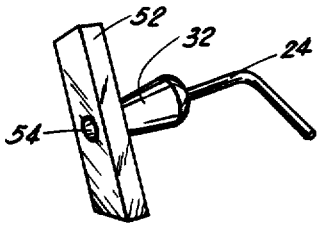
FIG. 6 is a partial perspective view of one of the illuminator means of the apparatus of FIG. 1 having a cushioning pad or skid adapted at the terminus thereof.
Figure 7:
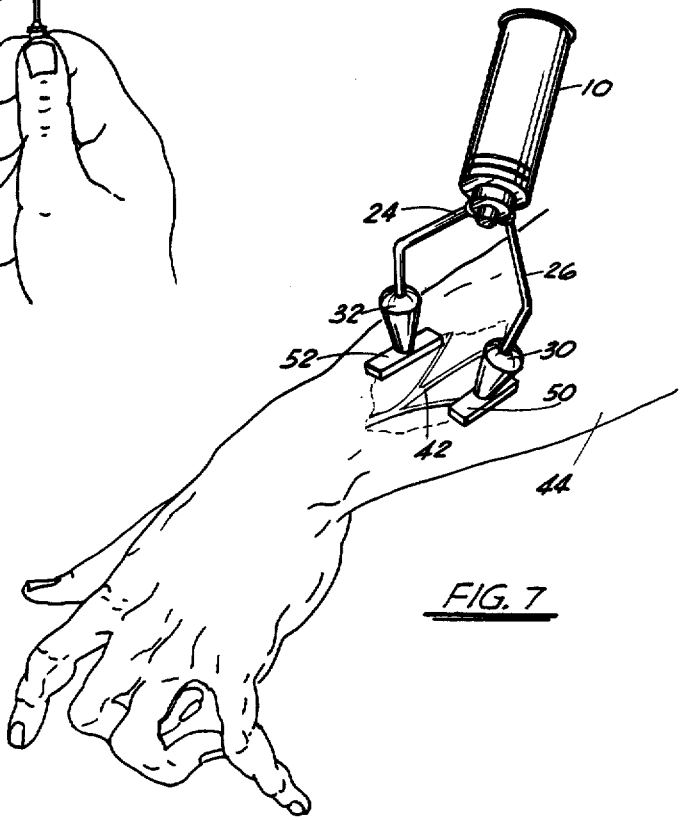
FIG. 7 is a perspective view of the apparatus of FIG. 6 in its preferred application.

Because hoods 30, 32 when mounted on the tissue of the individual to be inspected can slip and the skin must be taut and the underlying vein anchored for best results, rubber pads or skids 50, 52 can be applied to hoods 30, 32 respectively as illustrated in FIGS. 6 and 7. Each of skids 50, 52 would have an aperture 54 provided therethrough so that light can pass to the area to be inspected.

Figure 5:
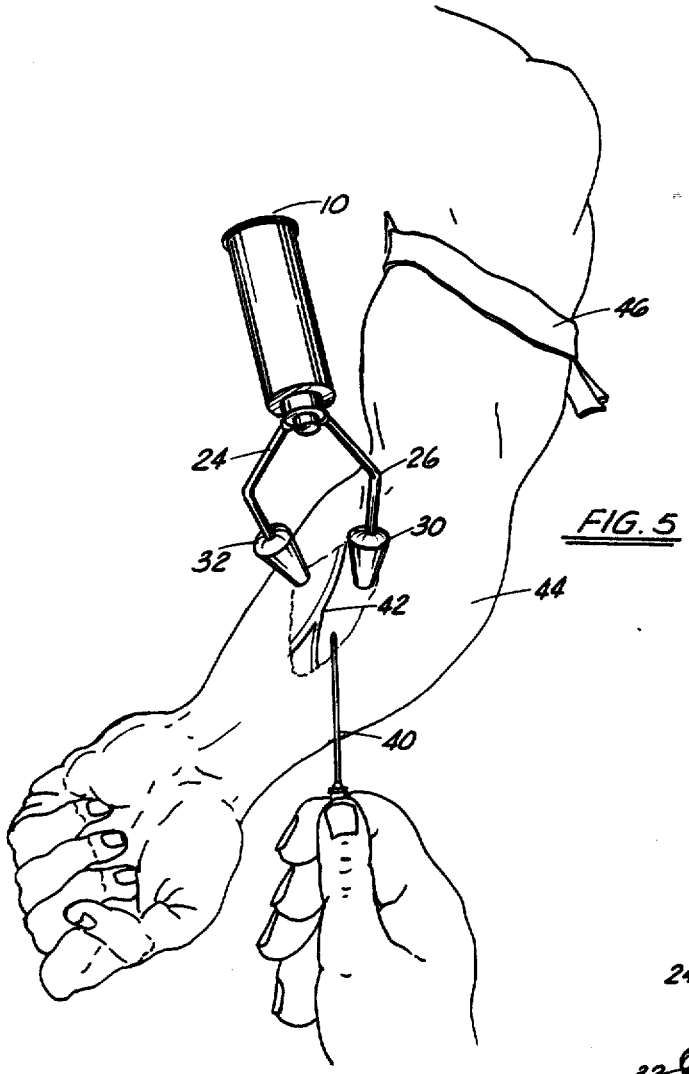
FIG. 5 is a perspective view of the apparatus of FIG. 1 in its preferred application.

The operation of apparatus 10, and apparatus 10 modified with skids or pads 50, 52 of FIGS. 6 and 7, is best seen in FIGS. 5 and 7. Housing 12 is grasped in one hand by the operator with his index finger or thumb having access to pen light switch 34. The halogen fiber optic lamps 31, 33 having hoods 30, 32 are placed in firm contact with the skin of the area to be inspected (lower arm 44 illustrated in FIGS. 5 and 7). (In the embodiment of apparatus 10 illustrated in FIGS. 6 and 7 skids or pads 50, 52 would be placed in firm contact with the skin area to be inspected). Next, rheostats 16, 18 are placed at or near their maximum intensity (POINT F) for an initial scan of limb 44 until a vein can be identified. (Of course this procedure works best in a dark environment, therefore all lights in the room should be turned off or set to their dimmest setting). Next, the angle of pivotal arms 24, 26 are set until the best image of the vein is produced. Arms 24, 26 are set by movement in the direction of ARROWS A, B, C or D as necessary by a rotation of each arm 24, 26 about swivel joint 25, 27. Once a vein 42 is identified, the level of intensity of each of lamps 31, 33 is adjusted by its respective rheostats 16, 18 until the best detail of vein 42 appears. Once the vein of interest 42 has been identified pressure can be exerted on the housing 12 which will cause the light hoods 30, 32 (or pads or skids 50, 52) to hold the skin taut and anchor vein 42 for intravenous introduction. For best results a tourniquet 46 can be placed on an extremity proximate to the area of interest.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A transcutaneous illuminating apparatus comprising:
   a. a housing having a source of electrical energy provided therein;
   b. means removably mounted on one end of said housing for pivotally supporting a plurality of tubular members at their proximate end, each of said tubular members having mounted on its distal end illuminating means;
   c. An electrical circuit including said source of [power] *electrical energy* and said illuminating means;
   d. means for selectively completing the circuit between said illuminating means and said source of electrical energy, thereby activating said illuminating means;
   e. means provided in said circuit for selectively varying the intensity of each of said illuminating means; and
   f. means for applying each of said illuminating means to the tissue area to be inspected.

2. The apparatus of claim 1 wherein said source of electrical energy is a battery.

3. The apparatus of claim 1 wherein said illuminating means is a halogen fiber optic light.

4. The apparatus of claim 1 wherein said means for selectively varying the intensity of each of said illuminating means is a rheostat provided in said circuit including said illuminating means and said source of electrical energy.

5. A transcutaneous illuminating apparatus comprising:
   a. a housing having a source of electrical energy provided therein;
   b. means removably mounted on one end of said housing for pivotally supporting plurality of elongaged tubular members at their proximate end, each of said tubular members having mounted on its distal end halogen fiber optic illuminating means;

c. an electrical circuit including said source of [power] *electrical energy* and said illuminating means;

d. means for selectively completing the circuit between said illuminating means and said source of electrical energy, thereby activating said illuminating means;

e. a rheostat provided in said circuit including said illuminating means and said source of electrical energy for selectively varying the intensity of each of said illuminating means; and f. means for applying each of said illuminating means to the tissue area to be inspected, said means including means for spacing said illuminating means from said tissue area.

*6. A transcutaneous illuminating apparatus comprising:*

*a. a housing receiving power thereinto from a source;*

*b. means mounted on one end of said housing for supporting a plurality of tubular members at their proximate end, each of said tubular members having mounted on its distal end illuminating means;*

*c. an electrical circuit between the source of power and said illuminating means;*

*d. means for completing the circuit between said illuminating means and said source of power, thereby activating said illuminating means;*

*e. means provided in said circuit for selectively varying the intensity of each of said illuminating means; and*

*f. means for applying each of said illuminating means to the tissue area to be inspected.*

*7. The apparatus of claim 6 wherein said power received is from a battery.*

*8. The apparatus of claim 7 wherein said illuminating means is a halogen fiber optic light.*

*9. The apparatus of claim 7 wherein said means for selectively varying the intensity of each of said illuminating means is a rheostat provided in said circuit including said illuminating means and said power received.*

*10. A transcutaneous illuminating apparatus comprising:*

*a. a housing;*

*b. means removably mounted on one end of the housing for pivotally supporting a plurality of elongated tubular members at their proximate end, each of the tubular members having mounted on its distal end fiber optic illuminating means;*

*c. a source of power to the illuminating means;*

*d. means for selectively completing a circuit between the illuminating means and the source of power, thereby activating the illuminating means;*

*e. means for selectively varying the intensity of each of the illuminating means; and*

*f. means for applying each of said illuminating means to the tissue area to be inspected, said means including means for spacing said illuminating means from said tissue area.*

*11. The apparatus in claim 10, wherein the source of power is electrical energy.*

*12. The apparatus in claim 10, wherein the means for varying the intensity of each of the illuminating means comprises a rheostat.*

*13. A transcutaneous illuminating apparatus comprising:*

*a. a housing;*

*b. at least a pair of tubular members pivotally mounted on a first end of the housing, each of the tubular members having mounted illuminating means thereon;*

*c. a source of light;*

*d. means for transmitting a light beam from the source of light to the illuminating means;*

*e. means for selectively varying the intensity of the beam light to the illuminating means; and*

*f. means for applying each of the illuminating means to the tissue area to be inspected.*

*14. A transcutaneous illuminating apparatus comprising:*

*a. a housing having a source of energy provided therein;*

*b. means mounted on one end of the housing for pivotally supporting a plurality of elongated tubular members at their proximate end, each of the tubular members having mounted on its distal end fiber optic illuminating means;*

*c. a circuit between the source of energy and the illuminating means;*

*d. means for selectively completing the circuit between the illuminating means and the source of energy, thereby activating the illuminating means;*

*e. means for selectively varying the intensity of light to the illuminating means; and*

*f. means for applying each of the illuminating means to the tissue area to be inspected.*

*15. The apparatus in claim 14, wherein the means for varying the intensity of the illuminating means comprises a rheostat.*

*16. The apparatus in claim 14, wherein the means for applying the illuminating means to the tissue area to be inspected further includes means for spacing the illuminating means from the tissue area.*

*17. The apparatus in claim 14, wherein the means for applying each of the illuminating means to the tissue area to be inspected further includes a pair of skids in firm contact with the skin of the area to be inspected in order to draw the skin taut around the area to be inspected.*

* * * * *